US005573785A

United States Patent [19]

Murphy

[11] Patent Number: 5,573,785
[45] Date of Patent: Nov. 12, 1996

[54] COSMETIC COMPONENT INCLUDING WATER SOLUBLE FIBER

[75] Inventor: Lawrence J. Murphy, Harvard, Ill.

[73] Assignees: R.I.T.A. Corporation, Woodstock, Ill.; Mountain Lake Manufacturing, Mountain Lake, Minn.

[21] Appl. No.: 393,047

[22] Filed: Feb. 23, 1995

Related U.S. Application Data

[63] Continuation of Ser. No. 966,637, Oct. 23, 1992, abandoned.

[51] Int. Cl.$^6$ ............................ A61K 7/075; A61K 7/40; A61K 7/48
[52] U.S. Cl. ........................... 424/70.1; 424/59; 514/23; 514/777; 514/847
[58] Field of Search ........................... 424/401, 59, 61, 424/65, 69, 70.1; 514/23, 772, 777, 773, 847

[56] References Cited

U.S. PATENT DOCUMENTS

| | | | |
|---|---|---|---|
| 4,138,479 | 2/1979 | Truscheit et al. | 424/92 |
| 4,182,751 | 1/1980 | Ayme | 424/92 |
| 4,337,243 | 6/1982 | Ayme | 424/92 |
| 4,343,784 | 8/1982 | Massot et al. | 424/45 |
| 4,695,549 | 9/1987 | Grabitz | 435/267 |
| 4,739,046 | 4/1988 | Di Luzio | 536/117 |
| 4,761,402 | 8/1988 | Williams et al. | 514/54 |
| 4,818,752 | 4/1989 | Williams et al. | 514/54 |
| 4,833,131 | 5/1989 | Williams et al. | 514/54 |
| 4,946,832 | 8/1990 | Goode et al. | 514/53 |
| 4,992,540 | 2/1991 | Jamas et al. | 435/255 |
| 5,019,391 | 5/1991 | Bunte et al. | 435/255 |
| 5,037,972 | 8/1991 | Jamas et al. | 435/255 |
| 5,082,673 | 1/1992 | Inglett | 426/21 |
| 5,082,936 | 1/1992 | Jamas et al. | 435/255 |
| 5,223,491 | 6/1993 | Donzis | 514/54 |
| 5,294,457 | 3/1994 | Jenkins | 426/573 |

FOREIGN PATENT DOCUMENTS

| | | |
|---|---|---|
| 0336899A3 | 10/1989 | European Pat. Off. |
| 4059717 | 2/1992 | Japan. |
| WO88/06880 | 9/1988 | WIPO. |

OTHER PUBLICATIONS

C. Burgaleta and D. W. Golde, Cancer Research, 37:1739–1742, Jun. 1977, "Effect of Glucan on Granulopoiesis and Macrophage Genesis in Mice".
Joyce K. Czop, Pathology and Immunopathology Research, 5:286–296, 1986, "The Role of β–Glucan Receptors on Blood and Tissue Leukocytes in Phagocytosis and metabolic Activation".
Jerold Z. Kaplan, Archives of Surgery, 119:1005–1008, Sep. 1984, "Acceleration of Wound Healing by a Live Yeast Cell Derivative".
William Goodson, David Hohn, Thomas K. Hunt and Daniel Y. K. Leung, Journal of Surgical Research, 21:125–129, 1976, "Augmentation of Some Aspects of Wound Healing by a 'Skin Respiratory Factor'".
W. Z. Hassid, M. A. Joslyn and R. M. McCready, Journal of the American Chemical Society, 63:295–298, Jan. 1941, "The Molecular Constitution of an Insoluble Polysaccharide from Yeast, *Saccharomyces cerevisiae*".
D. J. Manners, A. J. Masson and J. C. Patterson, Journal of General Microbiology, 80:411–417, 1974, "The Heterogeneity of Glucan Preparations from the Walls of Various Yeasts".
S. J. Leibovich and D. Danon, Journal of Reticuloendothelial Society, 27:1–11, 1980, "Promotion of Wound Repair in Mice by Application of Glucan".
Daniel N. Sauder, Dermatologic Clinics, 4:447–454, Jul. 1986, "Effect of Age on Epidermal Immune Function".
Jouni Uitto, Dermatologic Clinics, 4:433–446, Jul. 1986, "Connective Tissue Biochemistry of the Aging Dermis".
Konishi, H., et al., Chemical Abstracts, vol. 109, 1988, Abstract No. 215, 771G.
English Translation of Konishi, H., et al., Chemical Abstracts, vol. 109, 1988, Abstract No. 215, 771G.
Soap Cosmetics Chemical Specialties, vol. 70, No. 1, dated Jan. 1994, p. 109, "All–Natural Beta Glucan".
Cosmetics & Toiletries Magazine, vol. 110, dated Mar. 1995, pp. 63–64, 66, 68, and 70, David Paton et al., "Oats: Chemistry, Technology and Potential Uses in the Cosmetic Industry".

*Primary Examiner*—C. Warren Ivy
*Assistant Examiner*—Evelyn Huang
*Attorney, Agent, or Firm*—Marshall, O'Toole, Gerstein, Murray & Borun

[57] ABSTRACT

A cosmetic component is produced by dispersing in water a water-soluble fiber composed of about 4 to 6 weight percent beta glucan, about 1 to 5 weight percent fat, about 80 to 94 weight percent carbohydrates and less than 8 weight percent protein. The fiber composition forms a dispersion (e.g., a first paste or gel) with the hot water, which is mixed for about 1 to 5 minutes. Following mixing, the paste is cooled and then combined with one or more stable cosmetic components to form a cosmetic product. One novel cosmetic component useful with the invention is composed of: (a) about 4.0 to about 8.0 percent water by weight; (b) about 4.5 to about 5.5 percent beta-glucan by weight; (c) less than 8.0 percent protein by weight; (d) about 2.0 to 3.0 percent ash by weight; (e) about 1.0 to about 5.0 percent fat by weight; and (f) about 80 to about 94 percent carbohydrate by weight.

24 Claims, No Drawings

COSMETIC COMPONENT INCLUDING WATER SOLUBLE FIBER

This is a Continuation of U.S. application Ser. No. 07/966,637, filed Oct. 23, 1992, now abandoned.

BACKGROUND OF THE INVENTION

This invention relates generally to cosmetic compositions, and more specifically to the use of water-soluble fiber in cosmetic compositions.

Components of a cosmetic product must have certain qualities in order to be useful in a cosmetic product. For example, cosmetic compositions typically contain mineral oil and/or petroleum due to the beneficial or pleasant tactile effects or sensations that these compositions impart when placed on the skin.

In general, a cosmetic product must have a smooth, rich and lubricous feel that is not slick or greasy. A cosmetic product must be non-irritating. Depending on the final product, a cosmetic must possess ease of absorption into the skin and must meet certain viscosity requirements. A cosmetic must be easily rinsed off of skin with water. Also, typically a cosmetic must have (a) a minimal amount of tackiness both upon application to the skin and upon drying of the cosmetic, (b) a moist feel, and (c) lack of abrasiveness. The properties listed above may be called the "beneficial tactile effects" of a cosmetic product. Finally, a cosmetic must contain no pathogens or gram-negative bacteria, the principal causative agents of numerous well-known bacterial infections. A cosmetic product, in fact, must meet even more stringent requirements than food in this last regard.

Useful cosmetic components are desired for addition to cosmetics for other specific characteristics, in addition to tactile effects, that these components are able to impart. These attributes include, for example: suspension properties, emulsion stabilizing properties, and viscosity building properties.

Types of cosmetic products for which these properties are desirable include the following: lotions, make-up, hand cleaners, shampoos, hair conditioners, shave creams, moisturizers, after-shave lotions, acne preparations, cleansers, soaps, deodorant sticks, bath products, and other personal care products.

Suspension properties include the ability to uniformly disperse very small particles in a liquid medium. A cosmetic component useful for its ability to suspend solids must have the ability to suspend the solid requiring excessive viscosity. If excessive viscosity is required, this may render useless the cosmetic product for which the suspending agent is desired. In addition, the viscosity of useful components must not increase greatly over the long-term passage of time, as is encountered with many clays which are used for their suspending properties, in order to allow for a reasonable shelf life for the cosmetic product. The suspended solid or particles must also not tend to precipitate over the passage of time. Further, a useful component must have beneficial tactile effects when applied to the skin, must be temperature stable, and must not suppress the formation of foam in products where foam is desirable.

It has been attempted to use magnesium aluminum silicate or gels of carbomers as a suspending agent. However, in certain circumstances, results have been unsatisfactory because carbomers cannot be used due to the incompatibility of ionic cleansing agents with carbomer resins.

It is desirable to replace mineral oil and/or petroleum, typically found in cosmetic products, with other compounds because of the growing desire to offer consumers products that are "oil-free" and "fat-free" due to the negative manner in which oils are perceived by the public relating to health and beauty aids. In addition, mineral oil increases the clogging of skin pores, which may lead to the formation of skin eruptions or a condition known as "comedogenicity." Also, in the absence of mineral oil, a cosmetic product may afford greater water washability and attract less dirt onto the skin. Further, a cosmetic product lacking mineral oil or petroleum may also feel cleaner or lighter to the user.

Compounds such as esters, polyethylene glycol compounds, and corn oil have been utilized to avoid the use of mineral oil and/or petroleum. However, results with these compounds have been unsatisfactory for a number of reasons, including, at times, a higher cost based on a comparison of (a) finished-formula costs or (b) performance-level costs. Also, in certain instances, the above-mentioned compounds may require more careful formulation to obtain the requisite stability.

Silicone shampoos represent a recent development in the conditioning shampoo market. A useful conditioner, for example, must afford the hair advantageous wet combing and dry combing characteristics. However, silicones which condition the hair usually put demands on the shampoo system which may require compromises. For example, the silicone must remain dispersed throughout the shampoo over the shelf life of the product. This requires a carefully formulated system and may require special processing equipment. In addition, a useful shampoo must have a sufficient foaming ability. However, because silicone conditioners are foam suppressants, a silicone-containing shampoo has to be formulated to overcome this problem, and even with a formulation which attempts to compensate for the suppression of foam, in almost all products the foaming is likely to be compromised. A conditioning component must also have the beneficial properties discussed herein, including beneficial tactile effects and stability over the shelf life of the product.

SUMMARY OF THE INVENTION

It is an object of the invention to overcome one or more of the problems described above.

Accordingly, one object of the invention is to provide a cosmetic product having beneficial tactile effects and which lacks mineral oil and/or petroleum and/or effectively reduce the amount of mineral oil and/or petroleum required in a given formulation.

A further object of the invention is to provide a new and useful cosmetic component having beneficial suspension properties.

A still further object of the invention is to provide a new and useful cosmetic component which acts as an epidermal conditioner.

The invention relates to the production of cosmetic products generally, and more specifically, to the production of cosmetic products containing a water-soluble fiber based cosmetic component.

According to a method recited by the present invention, a cosmetic component is produced by first dispersing in hot water a water-soluble fiber composed of about 4 to 6 weight percent beta glucan, about 1 to 5 weight percent fat, about 80 to 94 weight percent carbohydrates, and less than about 8 weight percent protein. After the water-soluble fiber forms a dispersion (e.g., a first paste or gel) with the hot water, the dispersion is mixed for 1 to 5 minutes. Following mixing, the product is cooled and then combined with one or more other stable cosmetic components to form a cosmetic product.

The invention also recites a novel cosmetic component comprising: (a) about 4.0 to about 8.0 percent water by weight; (b) about 4.5 to about 5.5 percent beta-glucan by weight; (c) less than 8.0 percent protein by weight; (d) about 2.0 to 3.0 percent ash by weight; (e) about 1.0 to about 5.0 percent fat by weight; and (f) about 80 to about 94 percent carbohydrate by weight. It is contemplated within the scope of the invention that the water soluble of the cosmetic component may be modified by (a) propoxylation, (b) ethoxylation, (c) quarternization or (d) fatty acid condensation to enhance the fiber's cosmetic properties. It is expected that quarternization will facilitate the substantivity and static reduction of the cosmetic component, while propoxylation, ethoxylation and fatty acid condensation will enhance the surface wetting characteristics of the cosmetic components.

Other features and advantages are inherent in the methods and products claimed and disclosed or will become apparent to those skilled in the art from the following detailed description.

DETAILED DESCRIPTION OF THE INVENTION

The present invention discloses the production of a cosmetic product containing a water-soluble fiber cosmetic component. The cosmetic based component is produced in accordance with the invention from a suitable composition. Suitable fiber compositions for use with the present invention may be derived from a modified oat flour produced by the method disclosed in Inglett U.S. Pat. No. 5,082,673, the disclosure of which is incorporated herein by reference.

The fiber composition preferably used in conjunction with the invention is a mixed linkage of beta-glucan of oat endosperm which is unbranched polysaccharides composed of (1→4) and (1→3) linked beta-D-glucopyranosyl units of varying proportions. This polysaccharide is found in tissue of many cereals besides oat, including barley, rye grass, bamboo, mung bean, numerous lichens and a variety of different grasses. The composition of this polysaccharide generally is made up of approximately 70% 1→4 linked and 30% 1→3 linked beta-D-glucopyranosyl units. Whole oat flour is composed of about 3 to 4 weight percent fat, about 12 to 16 weight percent protein, with the balance being carbohydrate or starch.

The hydrolysis of oat flour (starch) involves the cleavage of the starch amylose and amylopectin chains with alpha-amylase at elevated temperatures. This reaction results in a fiber liquid fraction and an insoluble fiber protein, lipid complex. Upon completion of the reaction period, the enzyme is inactivated by either high temperature and/or low pH conditions. Starch of this nature occurs in a granular form. Starch granules are insoluble in cold water, but if they are disrupted by grinding they will swell in cold water and gel. If an intact starch granule is treated with warm water, a soluble portion of starch will diffuse out. In hot water the granules swell to a point that they burst. Generally, starch contains approximately 20% amylose, which is a water soluble fraction, and 80% amylopectin, which is water insoluble. However, when amylose and amylopectin are hydrolyzed with alpha-amylose, the resulting components are water insoluble, low molecular weight polysaccharides or maltose, D-glucose and B-glucan. After hydrolysis and enzyme inactivation, the insolubles are removed through centrifugation, leaving the soluble fraction rich in low dextrose equivalent maltodextrins and 5% B-glucan.

Oat gums which contain B-D-glucan have been identified as a potentially valuable industrial hydrocolloid and as an important dietary component with potential therapeutic value. Recent clinical and animal studies have shown the value of soluble oat fiber in regulating glucose metabolism and the reduction of serum cholesterol in humans.

According to the present invention, a cosmetic component is preferably produced by first dispersing in hot water a water-soluble fiber composition composed of about 4 to 6 weight percent beta glucan, about 1 to 5 weight percent fat, about 80 to 94 weight percent carbohydrates, and less than about 8 weight percent protein. After the water-soluble dispersion (e.g., a first paste or gel) forms a paste with the hot water, the dispersion is mixed for 1 to 5 minutes. Following mixing, the dispersion is cooled and then combined with one or more stable cosmetic components to form a cosmetic product.

In a preferred embodiment of the invention, the water-soluble fiber composition has the following composition:

TABLE I

| | |
|---|---|
| moisture | 4.0–8.0 wt. % |
| mineral (ash) | 2.0–3.0 wt. % |
| fat (ether extract) | 1.0–5.0 wt. % |
| protein | 0.1–8.0 wt. % max. |
| beta-glucan | 4.5–5.5 wt. % |

This fiber composition, typically in the form of a powder, has a talc-like feel and a color that is close to beige. The composition is easy to handle and store. In aqueous solution, the fiber composition is cloudy due to the trace of fat in its composition and has a brown or yellow tint. The odor of the fiber composition is pleasant, similar to the odor of oatmeal. The composition has a low microorganism count measure by a total plate count of less than 100 per gram, which is necessary for materials used in cosmetics. The fiber composition has no gram-negative bacteria and no pathogens.

The above-described fiber composition is commercially available from the Specialty Grain Products Company, a subsidiary of ConAgra, under the trade name TRIM CHOICE™. In preparing the cosmetic component of the invention, the fiber composition, in the form of a powder, is preferably dispersed in boiling water at a temperature of about 100° C (handling problems result at higher temperatures). This dispersion (e.g., a first paste or gel) is then mixed in a Waring blender for about 1 to 5 minutes, preferably about 2 minutes. This mixing process is a standard procedure performed with a commercially-available blender on medium-high speed. The hot water and mixing will form a first paste or gel.

After mixing, the first paste or gel may be chilled to about 4° C. (40° F.) or until a desired viscosity is achieved. Viscosity is preferably measured with a Brookfield Viscometer, which has a rotating spindle. Preferably, the viscosity will be between about 100 centipoise (very watery) and 200,000 centipoise (a hard paste), however the desired viscosity depends both on (a) the cosmetic product in which the final product will be utilized and (b) handling considerations. After this step, the product may be described as a "second paste, second gel" "fiber component" or a "cosmetic component."

The cosmetic component or fiber component is then combined with one or more stable cosmetic compounds to form a cosmetic product. It has been surprisingly found that when the fiber component is combined with one or more stable cosmetic compounds, the fiber component provides the cosmetic product with excellent tactile effects, and may be used as a substitute for oils, fats, waxes and petrolatum in cosmetic products.

Products which may be produced according to the present invention include the following: lotions, make-up, hand cleaners, shampoos, anti-dandruff shampoos, hair conditioners, shave creams, moisturizers, after-shave lotion, acne preparations, cleansers, soaps, deodorant sticks, bath products, and other personal care products. Products produced by the present invention have exhibited the following qualities: safety; non-irritating to the skin; cost-competitiveness; ease of formulation; suitable tactile effects; cleaner, lighter feeling than oil-based compositions; and the ability to suspend solids without precipitation following the passage of time.

As a food product, the fiber component is considered as "GRAS" ("Generally Regarded As Safe"). The fiber component produced according to the present invention is also safe for use in cosmetics. Topical application, as shown by repeat insult patch testing on humans, is non-toxic. The fiber component is also non-cytotoxic and non-irritating to the eye, as shown by testing with an in-vitro Advanced Tissue Sciences Skin Model ZK 1300. Ingestion of the fiber component is also non-toxic, as shown by feeding studies run on animals. In addition, the fiber component is non-irritating and non-sensitizing. The fiber component has also been tested by in-vitro skin model work.

The fiber useful with the invention is soluble in water, however, it forms cloudy solutions due to the small proportion of fat and protein present as part of its composition. The fiber is also soluble in glycerine at up to a concentration of 2 percent. A solution formed with glycerine is also cloudy. At levels exceeding 2 percent, the fiber begins to disperse itself in the glycerine with a proportional rise in viscosity.

The fiber composition of the present invention is referred to as RITAVENA 5 by the assignee of the application.

Table II illustrates the solubility of the fiber component in various solvents.

TABLE II

SOLUBILITY

| RITAVENA 5 | Solvents | | | | | | |
| --- | --- | --- | --- | --- | --- | --- | --- |
| Concentration (%) | Mineral Oil | Propylene Glycol | Corn Oil | Ethyl Alcohol | Isopropyl Alcohol | Glycerin | Water |
| 0.5% | Insoluble (precipitates) | Insoluble (precipitates) Whitish Haze | Insoluble (precipitates) | Insoluble (precipitates) | Insoluble (precipitates) Hazy | Soluble (With Haze) Thin, Faintly Yellow Gel | Soluble (With Haze) |
| 2% | Insoluble (precipitates) | Insoluble (precipitates) Whitish Haze | Insoluble (precipitates) | Insoluble (precipitates) | Insoluble (precipitates) Hazy | Soluble (With Haze) Thicker, Yellow Gel | Soluble (With Haze) |
| 10% | Insoluble (precipitates) | Insoluble (precipitates) Yellowish Haze | Insoluble (precipitates) | Insoluble (precipitates) | Insoluble (precipitates) Hazy | Dispersed Well Thick, Yellow-Orange Gel | Cloudy Gel |
| 20% | Insoluble (precipitates) | Insoluble (precipitates) Yellow-Orange Haze | Insoluble (precipitates) | Insoluble (precipitates) | Insoluble (precipitates) Hazy | Dispersed Well V. Thick Dark Yellow/Orange Gel | Cloudy Gel |

At room temperature, the viscosity of the aqueous fiber solution increases slightly up to a concentration of about 12 percent and then increases rapidly between concentrations of 12 percent and 25 percent. Table III illustrates the relationship of viscosity to concentration of a water solution of the fiber. It can be seen that a firmer gel forms when samples are allowed to equilibrate at the lower temperature.

TABLE III

| Concentration (% RITAVENA 5) | Viscosity (cps) (Cooled at 2° C.) | Spindle (RVF Brookfield) | Viscosity (cps) (Cooled at 4.4° C.) | Spindle (RVF Brookfield) |
| --- | --- | --- | --- | --- |
| .5% | 7.5 cps | #1 @ 20 | 8.75 cps | #1 @ 20 |
| 2% | 10.0 cps | | 13.75 cps | |
| 5% | 37.5 cps | | 67.5 cps | |
| 10% | 165 cps | | 185 cps | |
| 12.5% | 260 cps | | 325 cps | |
| 12.5% | 320 cps | TA @ 10 | 500 cps | TA @ 10 |
| 15% | 2,600 cps | | 4,400 cps | |
| 18% | 45,000 cps | TE @ 10 | | TE @ 10 |
| 20% | 50,000 cps | | 170,000 cps | |
| 25% | 265,000 cps | | 480,000 cps | |

The viscosity of a water solution of the fiber is also dependent upon temperature. A 20 percent water solution was prepared and viscosities were taken at various temperatures as the sample was allowed to warm from 4° C. to 37.8° C. The results are shown below in Table IV. All viscosities were run at the temperatures indicated on a Brookfield viscometer with spindle #TB at 10 rpm.

TABLE IV

| Temperature (°F.) | Viscosity (cps) |
| --- | --- |
| 40° | 28,500 |
| 60° | 27,200 |
| 70° | 25,200 |
| 100° | 16,800 |

Swelling of materials at refrigerated temperatures (4° C.) does not represent a practical approach for manufacturing purposes. Therefore, the time necessary to reach equilibrium viscosity by storage at room temperature was determined.

The equilibrium was reached after one week. The results from this study are shown in Table V. This work demonstrates that finished formula viscosities will be expected to increase with time over a seven day period before completely equilibrating. All viscosities were run at room temperature on a Brookfield RVF viscometer with spindle TE at 10 rpm.

TABLE V

A 25% solution comprising the cosmetic component of the present invention was made utilizing water warmed to 100° C. The solution was subsequently cooled to 25° C. Viscosities were taken @ 25° C. after 24 hour time periods.

| Hrs. | Viscosity (Cps) | |
|---|---|---|
| 24 | 116,250 | |
| 48 | 166,875 | 30% increase |
| 72 | 196,250 | 15% increase |
| 96 | 237,500 | 17% increase |
| 1 week | 272,500 | 12% increase |
| 1 week+ | stable | |

Three 20% solutions utilizing the fiber composition of the present invention were made utilizing water warmed to 100° C. The solutions were subsequently cooled at 4.4° C. for 3–4 hrs. One sample was then stored at each of the following three temperatures: 40°, 70°, and 110° F. Viscosities were read after 24 hour time intervals. All viscosities were run at temperature indicated (see Table VI).

TABLE VI

| Time (hrs) | Sample 1 40° F. | Sample 2 70° F. | Sample 3 110° F. |
|---|---|---|---|
| | Viscosities (cps) | | |
| 24 | 242,000 | 24,400 | 12,300 |
| 48 | 333,000 | 37,000 | 11,500 |
| 72 | 440,000 | 46,000 | 12,500 |

Viscosity is also dependent upon the pH of the water solution of the fiber of the present invention. Twenty percent fiber solutions were prepared at 100° C. and conditioned at 4° C. for 16 hours and then allowed to come to room temperature. Six samples were prepared at pH values indicated in Table VII. The viscosities were measured on a Brookfield RVF viscometer with spindle TC at 10 rpm. Within the range tested (4.6–8.8) the pH was not considered to have any real effect upon the viscosities of the systems. The results are shown in Table VII.

TABLE VII

| pH | Viscosity (cps) |
|---|---|
| 4.6 | 47,600 |
| 5.0 | 49,500 |
| 5.8 | 58,000 |
| 6.9 | 54,500 |
| 8.4 | 50,500 |
| 8.8 | 73,000 |

The fiber component described above may be combined with other stable cosmetic components to form various cosmetic products. There are at least three areas of application for the fiber component of the invention, which will now be described.

CATEGORY 1

Tactile Effects

The beneficial, novel tactile effects of the fiber component, i.e. the "feel" of the fiber component, will allow the fiber component to replace mineral oil, waxes, fats, petroleum, and other hydrocarbon-containing oils in cosmetic products, while still furnishing suitable tactile effects to the cosmetic product. The fiber component may be used at about 0.5 to 15.0 weight percent, preferably about 1 to 3 weight percent, based on the weight of the cosmetic product.

In a further embodiment of the present invention, the fiber component is used in conjunction with certain "carbomer" gels. A carbomer is an acrylate with cross-linking, and may be described as lacking cohesiveness with all other materials, including the carbomer itself. One such carbomer is sold commercially under the trade name of ACRITAMER® by the R.I.T.A. Corporation, the co-assignee of this application. Carbomers which may be used in accordance with the present invention include the following CTFA-designated carbomers: 940, 934 and 941, and preferably carbomer 940. Carbomer gels do not hold together well, and particles of gel will break apart from each other and will run off the skin. However, when the fiber component is used in conjunction with a carbomer for use in a cosmetic product, a gel results that has a much more cohesive and workable feel than that of a carbomer alone. The addition of the fiber also (a) increases the viscosity and (b) gives the mixture an excellent slip which has the feel of an emollient oil rather than a water based gum. In a further embodiment of the invention, the fiber component is used in conjunction with both a carbomer (at about 1%) and carboxy methyl cellulose (at about 0.1%).

A number of cosmetic products were made in accordance with the present invention in which the fiber component provided beneficial tactile effects after combination with one or more stable cosmetic components. The results are contained in Tables VIII–XIV.

In a very simple system, the cosmetic component (0.5 to 5.0% composition of "RITAVENA 5") was used in conjunction with 1% ACRITAMER 934 (Carbomer 934). The texture at 1% each of ACRITAMER 934 and RITAVENA 5 was similar by tactile observation to white petrolatum. By actual measurement with a Brookfield Viscometer, the petrolatum was found to be heavier. (See Table VIII.)

TABLE VIII

| | WATER BASED "PETROLATUM" | | |
|---|---|---|---|
| SAMPLE NO. | % ACRITAMER 934 | % RITAVENA 5 | VISCOSITY |
| 111-123 | 1.0 | 5.0 | 54,000 cps* |
| 111-106 | | | 60,000 cps* |
| 111-122 | 1.0 | 4.0 | 60,000 cps* |
| 111-109 | | | 58,000 cps* |
| 111-121 | 1.0 | 3.0 | 67,000 cps* |
| 111-108 | | | 64,000 cps* |
| 111-120 | 1.0 | 2.0 | 68,000 cps* |
| 111-107 | | | 66,000 cps* |
| 111-119 | 1.0 | 1.0 | 61,000 cps* |
| 111-47 | | | 56,000 cps* |
| 111-117 | 1.0 | 1.0 | 70,000 cps* |
| 111-101 | | | 66,000 cps* |
| 111-118 | 1.0 | 0.5 | 64,000 cps* |
| 111-102 | | | 63,000 cps* |

As compared to: PETROLATUM - (WITCO WHITE PROTOPET #1S) (viscosity = 130,000 cps)
*Spindle 7, Speed 20, RVF Brookfield The addition of RITAVENA 5 had many positive effects on the consistency of the 1% ACRITAMER 934 gel:

1. Added cohesiveness: Carbomer gels do not hold together well. Particles of gel will break apart from each other and the product will run off the skin. The addition of RITAVENA 5 makes the product cohesive. It adheres to itself and to surfaces which it comes in contact with.

2. Viscosity enhancement. There is an additive effect on viscosity between the ACRITAMER and the RITAVENA 5.

3. Slip. The resulting blends have excellent slip. They feel like a gel of emollient oil rather than a water based gum.

As a result of these benefits, the feel of oil based systems can be replicated or improved upon while maintaining the ease of rub out, lack of greasiness and water miscibility of the RITAVENA 5 systems.

A panel test was run on the gel described earlier with 1% RITAVENA 5 and 1% ACRITAMER 934 against petrolatum. Questions were asked about product preference. As shown in Table IX, it can be seen that the aqueous RITAVENA 5 gel was preferred in all areas. It is especially noteworthy that the RITAVENA 5 gel was preferred for feel and ease of application.

These effects seem to translate well to more sophisticated formulas. An emulsion facial cleanser was prepared with 8% mineral oil and compared with a non-mineral oil formula with 3% RITAVENA 5. The RITAVENA 5 system was preferred 75% to 25% over the mineral oil system with regard to:

which felt more luxurious which rinsed easier from the skin which lotion felt better after the skin was rinsed which lotion left the skin feeling better after it had dried.

TABLE IX

HAND LOTION PANEL TEST
(Aqueous Cream Vehicle)
Participants were asked: "Please evaluate the given hand lotions by applying them one at a time, and then answering the questions below:"
SAMPLE

|  | "Q" Petrolatum | "R" 1% ACRITAMER and 1% RITAVENA 5 Blend |
|---|---|---|
| 1) Which lotion felt more luxurious? | 0% | 100% |
| 2) Which lotion was easier to apply (to rub into the skin)? | 0% | 100% |
| 3) Which lotion had less tackiness when applied? | 0% | 100% |
| 4) Which lotion had less tackiness after drying? | 0% | 100% |
| 5) Which lotion felt better after drying? | 11% | 89% |
| 6) Appearance wise, which lotion do you prefer? | 0% | 100% |

Table X lists the composition of six samples of a novel moisturizer prepared in accordance with the present invention. Testing of the moisturizer samples showed satisfactory performance. In X-b and X-c, the moisturizers were characterized by the substantial absence of mineral oil. That is, the compositions contain less than 5% by weight mineral oil other than oil that was unintentionally or inadvertently added through addition of other components. In X-a, X-d, X-e and X-f, various amounts of mineral oil were added to the compositions to demonstrate the partial replacement of mineral oil in water in oil emulsion systems. The resulting compositions showed reduced greasiness with excellent feel and rub characteristics.

TABLE X

|  | X-a | X-b | X-c | X-d | X-e | X-f |
|---|---|---|---|---|---|---|
| Mineral Oil | 24.75 | — | — | 24.75 | 13.00 | 18.00 |
| Lanolin X-tra Deo | 5.00 | 5.00 | 5.00 | 5.00 | 5.00 | 5.00 |
| Octyl Dimethyl PABA | 0.50 | 0.50 | 0.50 | 0.50 | 0.50 | 0.50 |
| Beeswax | 3.00 | 3.00 | 3.00 | 3.00 | 3.00 | 3.00 |
| RITAVENA B5 | 1.50 | 1.50 | 5.00 | — | 1.50 | 5.00 |
| Borax | 0.25 | 0.25 | 0.25 | 0.30 | 0.30 | 0.50 |
| DL Panthenol | 0.10 | 0.10 | 0.10 | 0.10 | 0.10 | 0.10 |
| Sorbitan Monooleate | 0.80 | 0.80 | 0.80 | 0.80 | 0.80 | 0.80 |
| Color | 0.06 | 0.06 | 0.06 | 0.06 | 0.06 | 0.06 |
| Kathon CG | 0.20 | 0.20 | 0.20 | 0.20 | 0.20 | 0.20 |
| Distilled Water | 63.84 | 88.59 | 85.09 | 65.29 | 75.84 | 66.84 |
| Total | 100.00 | 100.00 | 100.00 | 100.00 | 100.00 | 100.00 |
| pH | 7.1 | — | — | 8.0 | 6.8 | — |
| Viscosity | 8500 cps* | — | — | 7,200 cps TB @ 10 Control | 59,000 cps TC @ 10 50% reduction | 28,000 cps TB @ 10 25% reduction |
| Stabilities: |  |  |  |  |  |  |
| 4° F. |  | separation |  |  |  |  |
| 40° F. |  | after 1 |  |  |  |  |
| 110° F. |  | cycle | — | — |  |  |
| Appearance |  | After 20 minutes at 5000 RPM slight separation | Very thin separates @ RT - looks curdled | Very thin separates @ RT - looks curdled |  |  |

TABLE X-continued

|  | X-a | X-b | X-c | X-d | X-e | X-f |
|---|---|---|---|---|---|---|
| Description of System | Without petrolatum with RITAVENA B5 (1.5%) | Without mineral oil and petrolatum with RITAVENA B5 (1.5%) | Without mineral oil and petrolatum with RITAVENA (5%) | | | |

*Spindle TA, Speed 10, RVF Brookfield

Table XI compares the composition and performance of a sample of a novel moisturizer prepared in accordance with the present invention with a control sample. The moisturizer sample demonstrates a system where the novel cosmetic component had a positive effect on the stability of the cosmetic product.

TABLE XI

|  | XI-a (Control) | XI-b |
|---|---|---|
| Distilled Water | 78.60 | 77.60 |
| RITAVENA B5 | — | 1.00 |
| Sorbitol 70% Soln. | 3.50 | 3.50 |
| Forlan 500 | 6.00 | 6.00 |
| Cetyl Alcohol | 0.70 | 0.70 |
| Mineral Oil | 8.00 | 8.00 |
| Stearic Acid | 2.00 | 2.00 |
| Methylparaben | 0.15 | 0.15 |
| Propylparaben | 0.05 | 0.05 |
| TEA (50%) | 1.00 | 1.00 |
| Total | 100.00 | 100.00 |
| pH | 7.9 | 8.0 |
| Viscosity Stabilities: | 3135 cps* | 4350 cps* |
| 4° F. | nc | nc |
| 40° F. | nc | nc |
| 110° F. | Separation after 1 week | Separation after 4 weeks |
| Description of System: | Oil no RITAVENA B5 | Oil 1% RITAVENA B5 |
| Centrifuge Results After 7 Min @ 1660 rpm 65 Min @ 3000 rpm | Slight separation | Tubes cracked |

*Spindle 3, Speed 20, RVF Brookfield

Table XII lists the composition and performance of three samples of a novel cleaner prepared in accordance with the present invention. The cleaner samples performed satisfactorily.

TABLE XII

|  | XII-a | XII-c | XII-c |
|---|---|---|---|
| Distilled Water | 81.50 | 82.50 | 73.50 |
| Patlac NAL | 0.50 | 0.50 | 0.50 |
| Pationic 138C | 8.00 | 8.00 | 8.00 |
| Pationic 122A | 2.00 | 2.00 | 2.00 |
| Mineral Oil | — | — | 8.00 |
| RITAVENA B5 | 2.00 | 1.00 | 2.00 |
| Ritapeg 150 DS | 0.50 | 0.50 | 0.50 |
| RITA EGDS | 3.00 | 3.00 | 3.00 |
| Methylparaben | 0.20 | 0.20 | 0.20 |
| Propylparaben | 0.10 | 0.10 | 0.10 |
| Supersat AWS-4 | 2.00 | 2.00 | 2.00 |
| Kathon CG | 0.20 | 0.20 | 0.20 |
| Total | 100.00 | 100.00 | 100.00 |
| pH | 6.3 | 6.5 | 6.4 |
| Viscosity Stabilities: | 33,500 cps* | 35,000 cps* | 23,000 cps* |
| 4° F. | | | |
| 40° F. | | | |
| 110° F. | | | |
| Description of System: | No oil 2% RITAVENA B5 | No oil 1% RITAVENA B5 | Mineral oil 2%; RITAVENA B5 |
| FOAM TESTING | Foam   H₂O | Foam   H₂O | Foam   H₂O |
| 0.0 Minutes | 215     90 | 175     90 | 100     100 |
| 1.0 Minute | 215     95 | 160     95 | 100     100 |
| 13.0 Minutes | 215     95 | 155     95 | 100     100 |

*Spindle TC, Speed 10, RVF Brookfield

Table XIII lists the composition of two samples of a novel cleanser prepared in accordance with the present invention.

This is an example of an application where hydrocarbon is replaced with the novel cosmetic component. The moisturizer samples performed satisfactorily and demonstrated improved foaming performance over a cosmetic product which contained mineral oil.

TABLE XIII

|  | XIII-a | XIII-b |
|---|---|---|
| Distilled Water | 73.50 | 80.50 |
| Patlac NAL | 0.50 | 0.50 |
| Pationic 138C | 8.00 | 8.00 |
| Pationic 122A | 2.00 | 2.00 |
| Corn Oil | 8.00 | — |
| RITAVENA B5 | 2.00 | 3.00 |
| Ritapeg 150 DS | 0.50 | 0.50 |
| RITA EGDS | 3.00 | 3.00 |
| Methylparaben | 0.20 | 0.20 |
| Propylparaben | 0.10 | 0.10 |
| Supersat AWS-4 | 2.00 | 2.00 |
| Perfume | 0.20 | — |
| Kathon CG | — | 0.20 |
| Total | 100.00 | 100.00 |
| pH | 6.3 | 6.4 |
| Viscosity | 12,500 cps* | 30,500 cps* |
| Stabilities: |  |  |
| 4° F. | nc | nc |
| 40° F. | nc | nc |
| 110° F. | nc | Separation after 3 weeks |
| Description of System: | Corn oil 2% RITAVENA B5 | No oil 3% RITAVENA B5 |
| FOAM TESTING | Foam  H₂O | Foam  H₂O |
| 0.0 Minutes | 120   95 | 200   90 |
| 1.0 Minute | 105   95 | 200   100 |
| 3.0 Minutes | 105   95 | 200   100 |

*Spindle TC, Speed 10, RVF Brookfield

Table XIV demonstrates the viscosity of two samples of the novel cosmetic product prepared in accordance with the present invention. The samples are compared with a petrolatum control product. This is a further example of replacing hydrocarbon with the novel cosmetic products.

TABLE XIV

| SAMPLE NO. | % ACRITAMER 934 | % RITA-VENA B5 | VISCOSITY |
|---|---|---|---|
| XIV-a | 1.0 | 1.0 | 70,000 cps* |
| XIV-b | 1.0 | 1.0 | 66,000 cps* |
| Control (Petrolatum) | — | — | 130,000 cps* |

*Spindle 7, Speed 20, RVF Brookfield

CATEGORY 2

Suspension Properties

According to another feature of the present invention, a cosmetic product may be produced in which the fiber component functions as a suspending agent after combination with one or more stable cosmetic compounds. Cosmetic products in which the fiber component is useful as a suspending agent include: liquid make-up, cleansers with abrasives, anti-dandruff shampoos and sunscreens.

The suspending properties of the fiber component allow suspension of the following solids: pigments, anti-dandruff agents, opacifiers and abrasives. More specifically, in accordance with the present invention, the following useful materials may be suspended: sulfur, walnut shells, titanium dioxide, selenium disulfide, iron oxides, aluminum oxides, pumice, make-up-pigments and zinc omadine.

According to a preferred embodiment of the present invention, an anti-dandruff shampoo is prepared wherein 2 to 4 weight percent, preferably 3 weight percent, fiber is used to suspend sulfur at 2 weight percent. Sulfur does not tend to precipitate out of the shampoo over the long term. According to a further embodiment of the present invention, a liquid eye shadow and liquid eye foundation may be prepared. The fiber component has the ability to suspend make-up pigment and also imparts beneficial tactile effects to the cosmetic product, including a moist, non-abrasive feel to the skin. In addition, as opposed to carbomer gels, the fiber component is compatible with ionic cleansing agents for use in shampoos and cleansers. When the fiber component is used in a cosmetic product, the fiber component has been found to be more effective as a suspending agent than carbomer gels.

A number of cosmetic products were produced in accordance with the present invention in which the fiber component functions as a suspending agent after combination with one or more stable cosmetic components. The results are contained in Tables XV–XVI.

Table XV lists the composition of three samples of a novel anti-dandruff shampoo prepared in accordance with the present invention. The samples performed satisfactorily in suspending sulfur, the active ingredient in the shampoo.

TABLE XV

|  | XV-a | XV-b | XV-c |
|---|---|---|---|
| Sodium Lauryl Sulfate | 51.70 | 51.70 | 51.70 |
| Distilled Water | 9.80 | 9.80 | 8.80 |
| Pationic ISL/85 | 3.00 | 3.00 | 3.00 |
| Ethylene Glycol Distearate | 3.00 | 3.00 | 3.00 |
| Cocamide DEA | 4.50 | 4.50 | 4.50 |
| Propylene Glycol | 2.00 | 2.00 | 2.00 |
| NaCl 25% Soln. | — | — | 1.00 |
| Lactic Acid (44%) | QS | QS | QS |
| Flowers of Sulfur | 2.00 | 2.00 | 2.00 |
| RITAVENA B5 | 4.00 | 4.50 | 4.50 |
| Distilled Water | 20.00 | 19.50 | 19.50 |
| Total | 100.00 | 100.00 | 100.00 |
| pH | 7.55 | 7.55 | 7.55 |
| Viscosity: | 5,500 cps* | 8,600 cps* | 15,800 cps* |
| Stability: |  |  |  |
| 4° F. |  |  |  |
| 40° F. |  |  |  |
| 110° F. | No separation |  | Slight separation but sulfur stays |
| FOAM TESTING | Foam  H₂O | Foam  H₂O | Foam  H₂O |
| 0.0 Minutes | 300   75 | 410   60 | 310   80 |
| 1.0 Minute | 300   95 | 410   100 | 310   100 |
| 3.0 Minutes | 290   95 | 410   100 | 295   100 |

*Spindle TA, Speed 10, RVF Brookfield

Table XVI lists the composition of three samples of a novel lotion hand cleaner with an abrasive prepared in accordance with the present invention. The moisturizer samples performed satisfactorily in suspending the abrasive solid.

TABLE XVI

|  | XVI-a | XVI-b | XVI-c |
|---|---|---|---|
| Distilled Water | 59.55 | 58.88 | 60.05 |
| Bioterge AS-40 | 25.00 | 25.00 | 25.00 |
| Methylparaben | 0.15 | 0.15 | 0.15 |
| Ritasynt IP | 4.00 | 4.00 | 4.00 |
| Pationic ISL | 3.00 | 3.00 | 3.00 |
| RITAPEG 150 DS | 1.00 | — | 0.50 |
| RITAVENA B5 | 2.00 | 2.00 | 2.00 |
| Walnut Shells (Coarse) | 5.00 | 5.00 | 5.00 |
| NaCl (25% Soln.) | — | 1.67 | — |
| Kathon CG | 0.10 | 0.10 | 0.10 |
| TEA (50% Soln.) | 0.15 | 0.15 | 0.15 |
| Perfume | 0.05 | 0.05 | 0.05 |
| Total | 100.00 | 100.00 | 100.00 |
| pH | 6.0 | 6.2 | 6.1 |
| Viscosity | 36,000 cps* | 400 cps* | 14,000 cps* |
| Foaming Results: | Foam   H$_2$O | Foam   H$_2$O | Foam   H$_2$O |
| 0.0 Minutes | 340     90 | 325     80 | 250     80 |
| 1.0 Minute | 340    100 | 325    100 | 250    100 |
| 3.0 Minutes | 335    100 | 325    100 | 250    100 |
| Stabilities: |  |  |  |
| 4° F. | NC after 3 cycles | Walnuts drop to bottom after 1 cycle | NC after 3 cycles |
| 40° F. |  | Walnuts drop to bottom after 24 hours |  |
| 110° F. | Separation overnight | Separation overnight | Separation overnight |
| 70° F. | No change overnight | No change overnight | No change overnight |
| Centrifuge Results: | Particles remain suspended after 10 seconds @ 1600 rpm | Most particles remain suspended after 10 seconds @ 1600 rpm | Most particles remain suspended after 10 seconds @ 1600 rpm |
| Description: | 1% RITAPEG 150 DS With 2% RITAVENA B5 | Without RITAPEG 150 DS With 2% RITAVENA B5 | With 0.5% RITAPEG 150 DS With 2% RITAVENA B5 |

*Spindle TA @ Speed 10, RVF Brookfield

CATEGORY 3

Conditioning Properties

A third feature or area of application for the fiber component is utilization of the unexpected conditioning properties of the fiber component. In accordance with the present invention, a cosmetic product may be produced wherein the fiber component functions as an epidermal conditioner after combination with one or more stable cosmetic components.

For example, in accordance with the present invention, hair conditioners and conditioning shampoos may be produced. The fiber component may be combined with detergents and thickeners to form a cosmetic product. Examples of stable cosmetic components with which the fiber component may be combined are: alcohol sulfates, ether sulfates, amides, polyethylene glycol esters and lactylates.

In a preferred embodiment of the invention, a shampoo product produced by the inventive method uses the fiber of the fiber component at about 2 weight percent in combination with additional cosmetic components. Because the fiber does not form clear solutions in water, a lotion-type shampoo, similar to those commercially-available such as Pert-Plus, is preferably utilized. As a result of the fiber component's excellent conditioning properties, shampoos produced by the inventive method exhibit (a) very good wet combing and dry combing characteristics, (b) beneficial tactile effects, and (c) satisfactory foaming properties. In another embodiment of the invention, the fiber component is used as a conditioning agent in conjunction with a silicone conditioning agent in a multiple-conditioner shampoo.

A number of novel silicone shampoos were produced in accordance with the present invention in which the fiber component functions as an epidermal conditioning agent after combination with one or more stable cosmetic components. The samples performed satisfactorily, and the results are contained in Tables XVII–XVIII.

TABLE XVII

|  | XVII-a | XVII-b | (Repeat of XVII-a) |
|---|---|---|---|
| Pationic 122A | 11.0 | 11.00 | 11.00 |
| PPG Masil SF 60,000 | 1.00 | — | 1.00 |

TABLE XVII-continued

|  | XVII-a | XVII-b | (Repeat of XVII-a) |
|---|---|---|---|
| RITAPEG 150 DS | 2.00 | 2.00 | 2.00 |
| EGDS | 3.00 | 3.00 | 3.00 |
| Propylparaben | 0.05 | 0.05 | 0.05 |
| Distilled Water | 43.10 | 44.10 | 43.10 |
| Bioterge AS-40 | 37.50 | 37.50 | 37.50 |
| Methylparaben | 0.15 | 0.15 | 0.15 |
| RITAVENA 5 | 2.00 | 2.00 | 2.00 |
| Kathon CG | 0.20 | 0.20 | 0.20 |
| Total | 100.00 | 100.00 | 100.00 |
| pH | 5.5 | 5.7 | 5.8 |
| Viscosity | 12,500 cps* | 12,500 cps* | 12,500 cps |
| Foaming Results: | Foam   H$_2$O | Foam   H$_2$O | Foam   H$_2$O |
| 0.0 Minutes | 275    75 | 340    75 | 310    90 |
| 1.0 Minute | 275    95 | 340    100 | 310    100 |
| 3.0 Minutes | 275    100 | 340    100 | 310    100 |
| Wet Combing | Slightly difficult | Slightly difficult | Difficult |
| Dry Combing | Easy | Easy, except where knots are | Easy |
| Stabilities: |  |  |  |
| 4° F. | No change after 3 cycles | No change after 3 cycles | No change after 3 cycles |
| 40° F. | No change after 6 weeks | No change after 2 weeks | No change after 2 weeks |
| 110° F. | Separation after 1 week | Separation after 24 hours | No change after 2 weeks |
| Centrifuge Results: | Separates after 10 min. @ 5000 rpm | Separates after 10 min. @ 5000 rpm | Not run |
| Description of System: | With Silicone with RITAVENA | Without Silicone with RITAVENA | With Silicone with RITAVENA |

*Spindle TC, Speed 10, RVF Brookfield

TABLE XVIII

|  | XVIII-a | XVIII-b |
|---|---|---|
| Pationic 138C | 8.00 | 8.00 |
| PPG Masil SF 60,000 | 1.00 | — |
| RITAPEG 150 DS | 2.00 | 2.00 |
| EGDS | 3.00 | 3.00 |
| WITCONATE SXS | 2.00 | 2.00 |
| Propylparaben | 0.05 | 0.05 |
| Distilled Water | 44.10 | 45.10 |
| Bioterge AS-40 | 37.50 | 37.50 |
| Methylparaben | 0.15 | 0.15 |
| RITAVENA 5 | 2.00 | 2.00 |
| Kathon CG | 0.20 | 0.20 |
| Total | 100.00 | 100.00 |
| pH | 6.4 | 6.7 |
| Viscosity | 24,000 cps* | 35,000 cps* |
| Foaming Results: | Foam   H$_2$O | Foam   H$_2$O |
| 0.0 Minutes | 310    80 | 370    75 |
| 0.1 Minute | 310    100 | 360    100 |
| 3.0 Minutes | 310    100 | 360    100 |
| Wet Combing | Very difficult | Very difficult |
| Dry Combing | Slightly difficult | Very easy |
| Stabilities: |  |  |
| 4° F. | No change after 3 cycles | No change after 3 cycles |
| 40° F. | No change after 6 weeks | No change after 2 weeks |
| 110° F. | No change after 6 weeks | No change after 2 weeks |
| Centrifuge Results: | Separates after 20 min. @ 5000 rpm | Not run |
| Description of System: | With Silicone with RITAVENA | No Silicone with RITAVENA |

*Spindle TC, Speed 10, RVF Brookfield

The foregoing detailed description has been given for clearness of understanding only, and no unnecessary limitations should be understood therefrom, as modifications will be obvious to those skilled in the art. For example, the features and advantages of the methods of the present invention can be adapted for the production of types of cosmetic and personal care products other than those products specifically disclosed.

I claim:

1. A cosmetic component produced by a method consisting essentially of the steps of:

a) placing a water-soluble fiber consisting essentially of about 4 to 6 wt. % modified or unmodified beta-glucan, about 1 to 5 wt. % fat, about 80 to 94 wt. % carbohydrates, and less than about 8 wt. % protein in hot water for a time sufficient to form a dispersion;

b) mixing said dispersion for time sufficient to form a gel; and c) cooling said gel to form a cosmetic component.

2. A cosmetic component as recited in claim 1 wherein:

said cosmetic component comprises about 4 to 8 wt. % moisture, about 2 to 3 wt. % minerals, about 0.1 to 8 wt. % protein, and about 4.5 to 5.5 wt. % beta-glucan.

3. A cosmetic component as recited in claim 1 wherein:

said component is characterized by the substantial absence of hydrocarbon-containing oil.

4. A method for preparing the cosmetic component of claim 1 for use in a cosmetic product, said method consisting essentially of the steps of:

a) placing a water-soluble fiber consisting essentially of about 4 to 6 wt. % modified or unmodified beta-glucan, about 1 to 5 wt. % fat, about 80 to about 94 wt. % carbohydrate, and less than about 8 wt. % protein in hot water for sufficient time to form a dispersion;

b) mixing said dispersion for time sufficient to form a gel; and c) cooling said gel to form said cosmetic component.

5. A method as recited in claim 4 wherein:

said hot water is at a temperature of about 50° C. to about 100° C.

6. A method as recited in claim 5 wherein:

said hot water is held at a temperature of about 100° C.

7. A method as recited in claim 4 wherein:

said mixing time in step (b) is about 1 to 5 minutes.

8. A method as recited in claim 4 wherein:

said gel is cooled until at a viscosity of about 100 cps to about 200,000 cps.

9. A method as recited in claim 4 wherein:

said gel is cooled at about 2° C. to 6° C.

10. A method as recited in claim 4 wherein:

said viscosity of said gel is increased in step (c) to about 50,000 cps to about 100,000 cps.

11. A method as recited in claim 4 wherein:
said water-soluble fiber is a powder.

12. A cosmetic component suitable for topical application consisting essentially of:
   a) about 4.0 to about 8.0 percent water by weight;
   b) about 4.5 to about 5.5 percent beta-glucan by weight;
   c) less than 8.0 percent protein by weight;
   d) about 2.0 to 3.0 percent ash by weight;
   e) about 1.0 to about 5.0 percent fat by weight;
   f) about 80 to about 94 percent carbohydrate by weight; and
   g) a cosmetic carrier.

13. A cosmetic component as recited in claim 1 wherein:
step (b) comprises mixing for about 1 to 5 minutes.

14. A method as recited in claim 7 wherein:
said mixing time in step (b) is about 2 minutes.

15. A method for preparing the cosmetic component of claim 12 for use in a cosmetic product and suitable for topical application, said method consisting essentially of the steps of:
   a) placing a water-soluble fiber consisting essentially of about 4 to 6 wt. % modified or unmodified beta-glucan, about 1 to 5 wt. % fat, about 80 to about 94 wt. % carbohydrate, and less than about 8 wt. % protein in hot water for sufficient time to form a dispersion;
   b) mixing said dispersion to form a gel;
   c) cooling said gel to form a cosmetic component suitable for topical application; and
   d) combining the product of step (c) with a conventionally acceptable topical carrier.

16. A method as recited in claim 15 wherein:
step (c) further comprises combining said gel, after cooling, with a carbomer.

17. A cosmetic component for use in a cosmetic product and suitable for topical application, said component produced by a method consisting essentially of the steps of:
   a) placing a beta-glucan containing water-soluble fiber in hot water for a time sufficient to form a dispersion;
   b) mixing said dispersion to form a gel; and
   c) cooling said gel to form a cosmetic component suitable for topical application.

18. A method for preparing the cosmetic component of claim 17 for use in a cosmetic product and suitable for topical application, said method consisting essentially of the steps of:
   a) placing a beta-glucan containing water-soluble fiber in hot water for a time sufficient to form a dispersion;
   b) mixing said dispersion to form a gel; and
   c) cooling said gel to form a cosmetic component suitable for topical application.

19. A method of suspending a water-insoluble compound in an aqueous composition, said method comprising the step of providing (a) said water-insoluble compound and (b) a sufficient amount of a suspending agent in said aqueous composition to suspend the water-insoluble compound, said suspending agent comprising:
   (a) about 4 to about 6 weight percent beta-glucan;
   (b) less than about 8 weight percent protein;
   (c) about 1 to about 5 weight percent fat; and
   (d) about 80 to about 94 weight percent carbohydrates.

20. A method of conditioning the hair comprising contacting the hair with a sufficient amount of the cosmetic component of claim 1.

21. A method of conditioning the skin comprising contacting the skin with a sufficient amount of the cosmetic component of claim 1.

22. A method of conditioning hair, comprising the steps of:
contacting the hair with a sufficient amount of a cosmetic composition comprising:
   (a) about 4 to about 8 weight percent moisture;
   (b) about 4 to about 6 weight percent beta-glucan;
   (c) less than about 8 weight percent protein;
   (d) about 1 to about 5 weight percent fat; and
   (e) about 80 to about 94 weight percent carbohydrates.

23. A method of suspending a water-insoluble compound in an aqueous composition, said method comprising the step of providing (a) said water-insoluble compound and (b) a sufficient amount of a suspending agent in said aqueous composition to suspend the water-insoluble compound, said suspending agent comprising:
   (a) about 4 to about 8 weight percent moisture;
   (b) about 4 to about 6 weight percent beta-glucan;
   (c) less than about 8 weight percent protein;
   (d) about 1 to about 5 weight percent fat; and
   (e) about 80 to about 94 weight percent carbohydrates.

24. A method of conditioning the skin, comprising the steps of:
contacting the skin with a sufficient amount of a cosmetic composition comprising:
   (a) about 4 to about 8 weight percent moisture;
   (b) about 4 to about 6 weight percent beta-glucan;
   (c) less than about 8 weight percent protein;
   (d) about 1 to about 5 weight percent fat; and
   (e) about 80 to about 94 weight percent carbohydrates.

* * * * *